United States Patent
Patil et al.

(10) Patent No.: US 10,934,518 B2
(45) Date of Patent: Mar. 2, 2021

(54) BIOREACTOR SYSTEM FOR CELL CULTIVATION

(71) Applicant: Global Life Sciences Solutions USA LLC, Marlborough, MA (US)

(72) Inventors: Haresh Digambar Patil, Bangalore (IN); Manoj Ramakrishna, Bangalore (IN); Anoop Bhargav, Bangalore (IN); Praveen Paul, Bangalore (IN); Sebastian John, Bangalore (IN); Swapnil Puranik, Bangalore (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 0 days.

(21) Appl. No.: 15/545,395

(22) PCT Filed: Jan. 29, 2016

(86) PCT No.: PCT/EP2016/051970
§ 371 (c)(1),
(2) Date: Jul. 21, 2017

(87) PCT Pub. No.: WO2016/124505
PCT Pub. Date: Aug. 11, 2016

(65) Prior Publication Data
US 2018/0002655 A1    Jan. 4, 2018

(30) Foreign Application Priority Data
Feb. 5, 2015   (IN) .............................. 335/DEL/2015

(51) Int. Cl.
*C12M 1/36*    (2006.01)
*C12M 1/00*    (2006.01)
(Continued)

(52) U.S. Cl.
CPC ......... *C12M 41/48* (2013.01); *B01F 11/0017* (2013.01); *B01F 15/0085* (2013.01);
(Continued)

(58) Field of Classification Search
CPC ...... C12M 41/48; C12M 23/04; C12M 23/14; C12M 23/38; C12M 23/52; C12M 27/16;
(Continued)

(56) References Cited

U.S. PATENT DOCUMENTS 4,923,449 A *  5/1990  Toya .................... A61M 1/0245
                                                    604/245
5,017,490 A *  5/1991  Taiariol .................. C12M 23/14
                                                    435/294.1
(Continued)

FOREIGN PATENT DOCUMENTS

WO    2005/111192 A1    11/2005
WO    2012/000502 A1     1/2012
(Continued)

OTHER PUBLICATIONS

PCT International Search Report and Written Opinion for PCT Application No. PCT/EP2016/051970 dated Apr. 13, 2016 (9 pages).
(Continued)

*Primary Examiner* — William H. Beidner
*Assistant Examiner* — Danielle B Henkel
(74) *Attorney, Agent, or Firm* — Eversheds Sutherland (US) LLP

(57) ABSTRACT

The present invention relates to a novel bioreactor system for cell cultivation. More specifically, the invention relates to a compact bioreactor system which has several integrated functions and enables small scale static culture as well as scale-up rocking culture in the same bioreactor. The bioreactor system comprises tray for positioning of a cell culture bag having adjustable volume, a lid covering the cell culture
(Continued)

bag and provided with heating function, an integrated perfusion unit, an integrated cell loading unit, and an integrated unit for automatic cell culture sampling, wherein the bioreactor system is controlled by a single control unit. The invention also relates to a method of cell culture using the bioreactor system for culture of therapeutic cells.

14 Claims, 2 Drawing Sheets

(51) Int. Cl.
  *C12M 3/06* (2006.01)
  *B01F 11/00* (2006.01)
  *C12M 1/34* (2006.01)
  *B01F 15/00* (2006.01)
  *C12M 1/12* (2006.01)
  *C12N 5/071* (2010.01)

(52) U.S. Cl.
  CPC ............ *C12M 23/04* (2013.01); *C12M 23/14* (2013.01); *C12M 23/38* (2013.01); *C12M 23/52* (2013.01); *C12M 27/16* (2013.01); *C12M 29/10* (2013.01); *C12M 41/12* (2013.01); *C12M 41/14* (2013.01); *C12N 5/0602* (2013.01); *C12N 2523/00* (2013.01); *C12N 2527/00* (2013.01)

(58) Field of Classification Search
  CPC ...... C12M 29/10; C12M 41/12; C12M 41/14; B01F 11/0017; B01F 15/0085; C12N 5/0602; C12N 2523/00; C12N 2527/00
  See application file for complete search history.

(56) References Cited

U.S. PATENT DOCUMENTS

| | | | |
|---|---|---|---|
| 8,889,406 B2* | 11/2014 | van der Heiden | B01F 11/0025 366/211 |
| 9,175,253 B2 | 11/2015 | Hata et al. | |
| 9,441,193 B2* | 9/2016 | Tanaka | C12M 23/14 |
| 9,714,408 B2* | 7/2017 | Tanaka | C12M 41/26 |
| 2010/0075406 A1* | 3/2010 | Tanaka | C12M 23/14 435/287.1 |
| 2010/0316446 A1 | 12/2010 | Runyon | |
| 2011/0035160 A1 | 2/2011 | Rhee et al. | |
| 2012/0258441 A1* | 10/2012 | Gebauer | C12M 23/14 435/3 |
| 2013/0109081 A1* | 5/2013 | Tsuchiya | C12M 23/12 435/286.1 |
| 2013/0157353 A1* | 6/2013 | Dijkhuizen Borgart | C12M 23/14 435/297.2 |
| 2013/0316446 A1 | 11/2013 | Andersson et al. | |
| 2016/0152935 A1* | 6/2016 | Roosloot | C12M 23/14 435/297.1 |

FOREIGN PATENT DOCUMENTS

| | | |
|---|---|---|
| WO | 2012/115586 A1 | 8/2012 |
| WO | 2015/009153 A1 | 1/2015 |

OTHER PUBLICATIONS

Japanese Office Action for JP Application No. 2017-539614 dated Oct. 11, 2019 (6 pages with English translation).
Chinese Office Action for CN Application No. 201680008907.X dated Sep. 3, 2020 (14 pages with English translation).

* cited by examiner

FIG 5
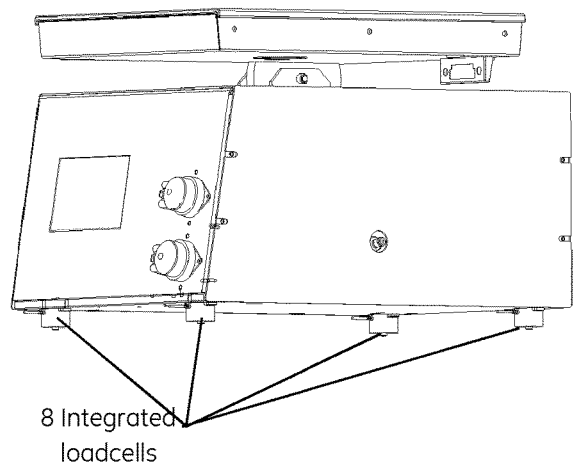
8 Integrated loadcells
FIG 6
FIG 7
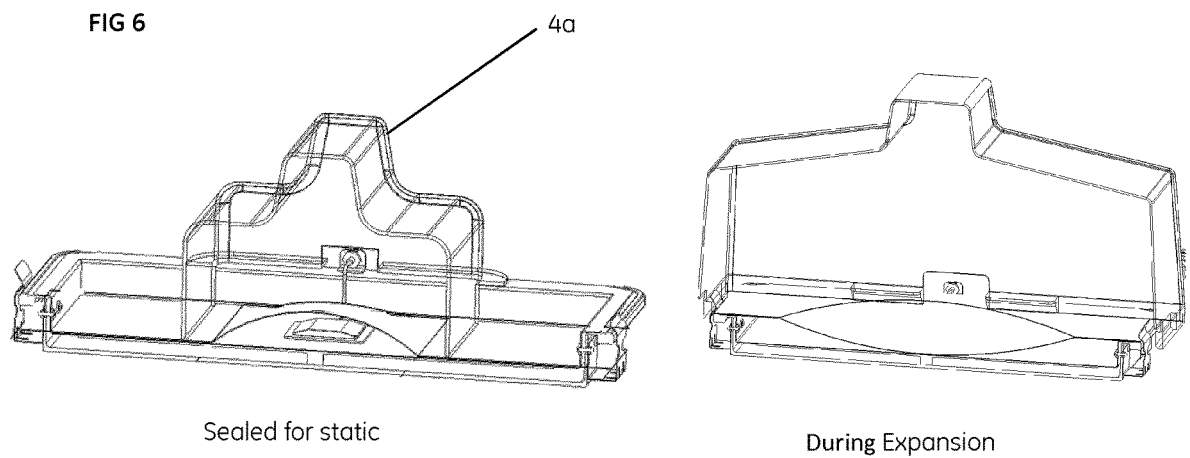
4a
Sealed for static
During Expansion

BIOREACTOR SYSTEM FOR CELL CULTIVATION

CROSS REFERENCE TO RELATED APPLICATIONS

This application claims the priority benefit of PCT/EP2016/051970 filed on Jan. 29, 2016 which claims priority benefit of Indian Application No. 335/DEL/2015 filed Feb. 5, 2015. The entire contents of which are hereby incorporated by reference herein.

FIELD OF THE INVENTION

The present invention relates to a novel bioreactor system for cell cultivation. More specifically, the invention relates to a compact bioreactor system which has several integrated functions and enables small scale static culture as well as scale-up rocking culture in the same bioreactor.

BACKGROUND OF THE INVENTION

Cell therapy is a new but rapidly expanding field in biotechnology which involves the administration of autologous or allogeneic cells that carry out a therapeutic effect in vivo. The adoptive T cell transfer protocols in the allogeneic hematopoietic stem cell transplant (HSCT) setting are on the premise that peripheral blood contained T cells to be able to mediate antitumor and/or antiviral activity in the HSCT recipient.

Hematopoietic stem cell transplantation (HSCT) is the transplantation of multipotent hematopoietic stem cells, usually derived from bone marrow, peripheral blood, or umbilical cord blood. It may be autologous (the patient's own stem cells are used) or allogeneic (the stem cells come from a donor). It is a medical procedure in the fields of haematology, most often performed for patients with certain cancers of the blood or bone marrow, such as multiple myeloma or leukaemia. In these cases, the recipient's immune system is usually destroyed with radiation or chemotherapy before the transplantation.

Adoptive cell transfer can refer to the transfer of cells, most commonly immune-derived cells, back into the same patient or into a new recipient host with the goal of transferring the immunologic functionality and characteristics into the new host. If possible, use of autologous cells helps the recipient by minimizing graft-versus-host disease (GVHD) issues.

In T cell-based therapies, these cells are expanded in vitro using cell culture methods relying heavily on the immunomodulatory action of interleukin-2 and returned to the patient in large numbers intravenously in an activated state. Anti-CD3 antibody is commonly used to promote the proliferation of T cells in culture. Research into interleukin-21 suggests it may also play an important role in enhancing the efficacy of T cell based therapies prepared in vitro. An emerging treatment modality for various diseases is the transfer of stem cells to achieve therapeutic effect. Clinically, this approach has been exploited to transfer either immune-promoting or tolerogenic cells (often lymphocytes) to patients to either enhance immunity against viruses and cancer or to promote tolerance in the setting of autoimmune disease, such as Type I diabetes or rheumatoid arthritis. Cells used in adoptive therapy may be genetically modified using recombinant DNA technology to achieve any number of goals. One example of this in the case of T cell adoptive therapy is the addition of chimeric antigen receptors, or CARs, to redirect the specificity of cytotoxic and helper T cells.

The adoptive transfer of autologous tumour infiltrating lymphocytes (TIL) or genetically re-directed peripheral blood mononuclear cells has been used to successfully treat patients with advanced solid tumours, including melanoma and colorectal carcinoma, as well as patients with CD19-expressing hematologic malignancies.

Tumour infiltrating lymphocytes (TILs) are a type of white blood cell found in tumours. TILs are implicated in killing tumour cells, and the presence of lymphocytes in tumours is often associated with better clinical outcomes. Several clinical trials have been conducted using TILs to treat patients with metastatic melanoma, a deadly form of skin cancer. Tumour reduction of 50% or more was observed in about half of melanoma patients treated with TILs. Some patients experienced complete responses with no detectable tumour remaining years after TIL treatment.

Clinical trials using TILs to treat digestive tract cancers, such as colorectal cancer, and cancers associated with the human papilloma virus (HPV), such as cervical cancer, are ongoing. Scientists are also investigating whether TILs can be used to treat other tumours, including lung, ovarian, bladder, and breast.

Adoptive T cell therapy involves the isolation and ex vivo expansion of tumour specific T cells to achieve greater number of T cells than what could be obtained by vaccination alone. The tumour specific T cells are then infused into patients with cancer in an attempt to give their immune system the ability to overwhelm remaining tumour via T cells which can attack and kill cancer. There are many forms of adoptive T cell therapy being used for cancer treatment; culturing tumour infiltrating lymphocytes or TIL, isolating and expanding one particular T cell or clone, and even using T cells that have been engineered to potently recognize and attack tumours.

Recent years have seen clinical trials show signs of success and products such as Prochymal (Osiris Therapeutics Inc.) and ChondroCelect (TiGenix) gain regulatory approval. However, many new cell therapies are treating relatively small numbers of patients so a universal system for delivery of these products from the site of manufacture to the clinic has not yet been established. It still needs to explore whether a universal system is realistic and explore the options for delivery of a cell therapy product to the clinic. It also highlights some of the challenges that still face the industry in this regard which need to be tackled if these therapies are to be adopted more widely Cell therapy involves a number of mandatory stages from cell collection to cell injection into a patient. Cell culturing for cell therapy is carried out in clean room environment. Cell culturing and clean rooms has many mandatory regulations like particle size and count in clean room, number of patient samples handled at a time as well as number of instruments per suite and sterile environment etc.

Currently available systems for cell culture are stand alone, require large space and cannot handle multiple patient samples at same time. Current procedures for cell culturing for cell therapy involve a lot of human intervention, which may contaminate cell cultures and damage cell growth, especially small size cell cultures. Thus, there is a need of better bioreactor systems.

SUMMARY OF THE INVENTION

The present invention provides a bioreactor which is compact in size and comprises a single system to control a number of instruments which means optimum utilization of clean room space.

Thus, in a first aspect the invention relate to a bioreactor system (1) for cell culture, comprising a tray (2) for positioning of a cell culture bag (3) having adjustable volume, a lid (4) covering the cell culture bag and provided with heating function, an integrated perfusion unit (5, 6), an integrated cell loading unit (8), and an integrated unit for automatic cell culture sampling, wherein the bioreactor system is controlled by a single control unit.

The tray (2) is movable and enables static as well as rocking cell culture at a desired rpm. Optionally several trays (2), such as 2-5, are present and stacked in a vertical direction on the bioreactor system. Each tray can hold at least one cell culture bag. Optionally the tray(s) is/are provided with barcode reader(s) and the cell bag(s) is/are provided with barcode(s).

The volume of the cell culture bag (3) may be increased from for example 50 mL to 3000 mL. This may be done by automatic clamping of the cell bag to the desired volume. The clamping may also be done by the lid as will be described in the detailed section.

In a preferred embodiment the inside of the top of the lid (4) is provided with heating elements. This will form an incubator like environment when the lid is closed on top of the tray and enclosing the cell culture bag.

Preferably the integrated perfusion unit comprises a media supply bag (5) and waste bag (6) and respective conduits for connection to the cell bag (3) and pumps driving said media into said bag and waste out of said bag. The integrated cell loading unit (8) preferably comprises a platform assembled with compression type load-cells having the ability to take the entire weight of the system.

In one embodiment the bioreactor system is movable and comprises an attachable cart (7) making the whole compact bioreactor system movable.

In a further embodiment multiple, such as 2-5, bioreactor systems are stacked on each other in vertical direction.

The multiple bioreactor systems will be controlled with single control unit, with flexibility of monitoring and controlling remotely from personal computer or mobile devices.

In a second aspect, the invention relates to a method for cell culture, comprising culturing of a starting cell culture in a bioreactor as above in a stationary state, wherein the volume of the cell culture bag is set to 50-500 mL and the culture is heated to 37° C., and then after 1-6, preferably 3-4 days, expanding the bag volume to 1500-3000 mL and continue the culturing in room temperature and under a rocking motion, wherein both the starting and continued culture is performed in the same cell culture bag and on the same bioreactor system. Preferably the starting cell culture volume is 30-350 mL and the scale up culture volume is 500-1500 mL which is suitable for a cell culture bag with a maximum volume of 2000 mL.

Preferably the starting cell culture is selected from stem cells, such as human hematopoietic stem cells, immune derived cells, such as T-cells or NK-cells, tumour infiltrating cells (TILs) or any other cells suitable for cell therapy.

BRIEF DESCRIPTION OF THE DRAWINGS

FIG. 5 is a schematic view of and integrated cell loading unit of the bioreactor system.

FIG. 6 shows the lid covering the cell bag in a shape suitable for static culture of small cell cultures.

FIG. 7 shows the lid covering the cell bag in a shape suitable for rocking culture of scale-up cell cultures.

DETAILED DESCRIPTION OF THE INVENTION

The novel bioreactor of the invention provides static as well as rocking cell culture and the user may select the most appropriate option for the particular cell culture. For example static culture is usually desired for small volume start up cultures while rocking culture is desired for larger production volumes.

The invention also enables scale out from small volume to large volume by enlarging the cell bag volume, i.e. a single bag is used for both small and scale-up culture. A certain volume of the single size bag will be closed and separated from rest of the volume for small volume static culture. Once static culture phase completes, the closed small volume will be opened allowing culture to occupy up to the complete bag volume for scale-up of culture.

The bioreactor provides, inter alia, integrated rocking, perfusion and media addition as well as controlled heating of the cell culture. A new heating method is provided which will eliminate losses of small size culture due to evaporation and condensation. Environmental conditions like temperature and gases in the cell culture bag will be maintained and controlled like an incubator under the lid of the bioreactor of the invention. Unlike existing heating pad type temperature control which has the potential threat of cooking cells during static phase, the bioreactor of the invention will provide heating similar to an incubator by providing heating control with hot air circulation while maintaining air temperature in a closed environment enclosed by the lid covering the cell bag.

Furthermore the possibility of remote monitoring and controlling will reduce physical administration of the cell culture process and avoids contamination caused by entering the clean room.

Figure 1:
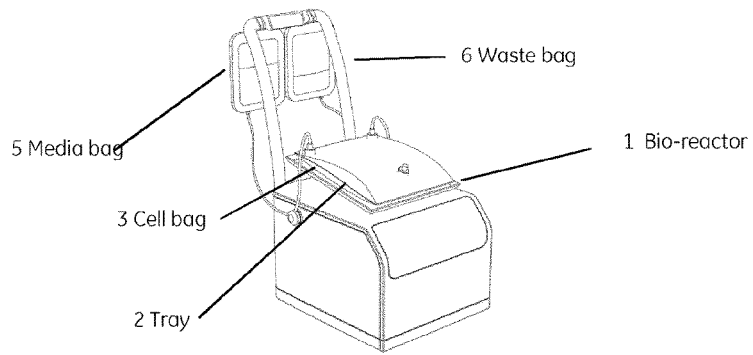
FIG. 1 is a schematic view of the bioreactor system of the invention wherein the lid or cover of the cell culture bag is removed.
Figure 2:
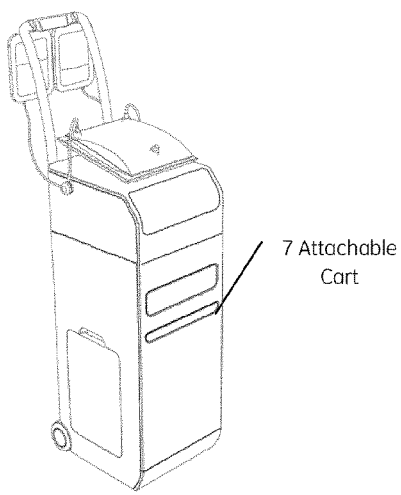
FIG. 2 is a schematic view of the bioreactor system as in FIG. 1 but provided with an attachable cart.

FIG. 1-2 show the bioreactor system 1 in an open condition wherein the cover or lid 4 is removed and the culture bag 3 and its connections to the media feed 5 and waste bag 6 are shown. The lid 4 will be placed back over the culture bag 3 on the tray 2 to maintain temperature and restrict falling of light on culture. The tray 2 is controlled to a stationary or racking state.

As shown in FIG. 2 the compact bioreactor system can be mounted on a cart 7 for mobility. The bioreactor can be easily moved with help of the cart within or outside the cleanroom. The cart can be loaded with all necessary accessories and consumables to be used for cell culturing.

Figure 3:
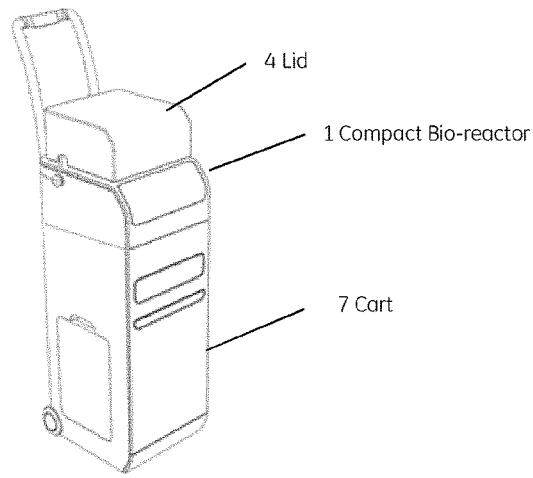
FIG. 3 is a schematic view of the bioreactor system as in FIG. 2 wherein the lid or cover is placed over the cell culture bag.

FIG. 3 shows the bioreactor placed on a cart with the lid 4 closed. The lid 4 encloses the cell culture bag 3 and rests against the tray 2 to form an enclosed space, like an incubator for the cell culture bag 3. The inside of the lid 4 is provided with controllable heating for example with hot air circulation.

Figure 4:
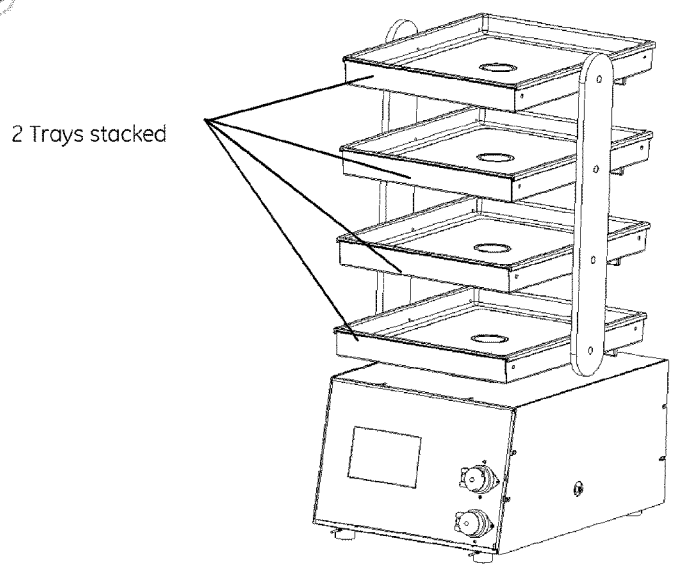
FIG. 4 is a schematic view showing several trays of the bioreactor stacked on top of each other.

The bioreactor of the invention can handle multiple patient samples at a time by tray stacking. As shown in FIG. 4 several trays may be arranged in parallel over the first tray, such as 2-5, each having the same properties as the as first tray in respect of for example rocking ability and positioning of cell bag. Stacked trays will isolate each sample with independent operational conditions. In the case of stacked trays, one common lid will be place over all present trays.

Preferably the tray 2 is provided with barcode reader and the cell bags 2 are provided with barcodes. The cell bags barcode will be recorded with patient details and tray barcode reader will read cell bag barcode for traceability of patient cells.

The compact bioreactors can also stack on each other as a standalone instrument, so that advantage of vertical space can be taken to reduce foot print.

Furthermore the bioreactor system of the invention is provided with an integrated cell loading unit 8 as shown in FIG. 5. The integrated cell loading unit 8 reduces overall size of the bioreactor system and helps monitor volume during perfusion.

During cell expansion the cells have to go through an initial static phase for 3-4 days under controlled environment of temperature and gases. In prior art static phase is performed in incubators and following cell expansion in static phase, cultured cells are taken out from the incubators and transferred from t-flask or small bags to large volume bag for scale-up. In the present invention the static culture is performed in a smaller volume of the cell culture bag 3 and the scale-up culture is performed within the same bag but an enlarged version thereof. During static culture the tray 2 will be in stationary condition and the lid 4 will be closed. During scale up culture the tray 2 will be in rocking motion and the lid 4 may be closed or opened according to the culture needs.

In FIGS. 6 and 7 it is shown how the lid 4 may control the volume of the cell culture bag 3. The small volume of the cell culture bag may be controlled by the lid 4 which may restrict the volume of the cell culture bag 3. As shown in FIG. 6, the lid 4a may be of smaller size than the regular lid 4 shown in FIG. 7. The edges of lid 4a restrict the volume of a one size, for example 2 L, bag to a smaller volume, such as 300 mL suitable for static culture. When the lid 4a is closed and placed against the cell bag 3 under pressure it will restrict the volume of the cell bag to a desired size. In FIG. 7 the lid 4 is a regular size lid without volume restricting function suitable for use during expansion of a 2 L culture. If a smaller scale-up culture than 2 L is used, such as 500-1000 mL, then a lid adapted to this culture volume will be used, i.e. a lid that restricts off the desired culture volume.

Post static culture phase, the restricted volume of bag will be released by removing lid 4a and allowing scale up to 2 L. Via tubing, the media bag 5 will fill the cell bag 3 with media and tray 2 will rock for cell growth. The waste bag 6 will via tubing collect waste from the cell bag 3 during perfusion.

During cell culture it is important to monitor cell growth and this is mainly based on pH, dissolved oxygen (DO), and cell density. pH and DO can be monitored with sensors which are not in contact with the culture, such as conventional optical sensors, but for cell density samples need to be taken periodically from the culture. In the present bioreactor an integrated auto sampling sub system will collect sample and separate each sample.

The invention claimed is:

1. A bioreactor system for cell culture, comprising:
   a cell culture bag defining an adjustable volume therein,
   an adjustable clamp in communication with the cell culture bag for regulating the volume of the cell culture bag,
   a tray for positioning of the cell culture bag,
   a removable lid having a top and an inside covering the cell culture bag, wherein the inside of the top of the lid is provided with an enclosed heating control system with hot air circulation in an enclosed environment,
   an integrated perfusion unit,
   an integrated cell loading unit, and
   an integrated unit for automatic cell culture sampling, wherein the bioreactor system is controlled by a single control unit, and wherein the adjustable volume of the cell culture bag is increased from a first-static culture volume to a larger scale-up culture volume by adjustment of the clamp to open the cell culture bag to a larger volume.

2. Bioreactor system according to claim 1, wherein the tray is movable and enables static as well as rocking cell culture at a desired rpm.

3. Bioreactor system according to claim 1, wherein several trays, are present and stacked in a vertical direction on the bioreactor system.

4. Bioreactor system according to claim 1, wherein the volume of the cell culture bag may be increased from 50 mL to 3000 mL by adjusting the clamp.

5. Bioreactor system according to claim 1, wherein the integrated perfusion unit comprises a media supply bag and waste bag and respective conduits for connection to the cell culture bag and pumps driving said media into said cell culture bag and waste out of said cell culture bag.

6. Bioreactor system according to claim 1, wherein the bioreactor system is movable and comprises an attachable cart.

7. Bioreactor system according to claim 1, wherein the integrated cell loading unit comprises a platform assembled with compression load-cells taking entire weight of the system.

8. Bioreactor system according to claim 1, wherein the tray(s) is/are provided with barcode reader(s) and the cell bag(s) is/are provided with barcode(s).

9. Bioreactor system according to claim 1, wherein multiple, bioreactor systems are stacked on each other in vertical direction.

10. Bioreactor system according to claim 9, wherein the multiple bioreactor systems are controlled with single control unit, with flexibility of monitoring and controlling remotely from personal computer or mobile devices.

11. Method for cell culture, comprising culturing of a starting cell culture in a bioreactor according to claim 1 in a stationary state, wherein the volume of the cell culture bag is set to 50-500 mL and the culture is heated to 37° C., and then after 1-6 days expanding the bag volume to 1500-3000 mL and continue the culturing in room temperature and under a rocking motion for scale up of the culture, wherein both the starting and scale up culture is performed in the same cell culture bag and on the same bioreactor system.

12. Method according to claim 11, wherein the starting cell culture is selected from stem cells, immune derived cells, tumour infiltrating cells (TILs) or any other cells suitable for cell therapy.

13. Bioreactor system of claim 1, wherein the clamp is provided on the lid to restrict the volume of the cell culture bag or to increase the volume of the cell culture bag.

14. Bioreactor system according to claim 1, wherein the clamp is automated for adjustment to increase the volume of the cell culture bag by the control unit.

* * * * *